United States Patent [19]

Romans-Hess et al.

[11] Patent Number: 4,655,759
[45] Date of Patent: Apr. 7, 1987

[54] REDUCED LEAKAGE MENSTRUAL PAD WITH BUILT-IN FOLD LINES

[75] Inventors: Alice Y. Romans-Hess, Fremont; Frederick M. Guenther, Oshkosh; Lenore S. Ryan, Appleton, all of Wis.

[73] Assignee: Kimberly-Clark Corporation, Neenah, Wis.

[21] Appl. No.: 777,887

[22] Filed: Sep. 19, 1985

[51] Int. Cl.⁴ ............................................. A61F 13/16
[52] U.S. Cl. ................................................ 604/385 R
[58] Field of Search ............... 604/385, 379–380, 604/383, 386–387, 400, 385 A, 358

[56] References Cited

U.S. PATENT DOCUMENTS

| | | | |
|---|---|---|---|
| 2,064,431 | 12/1936 | Jurgensen | 128/290 |
| 2,787,271 | 4/1957 | Clark | 128/290 |
| 3,395,201 | 7/1968 | Kalwaites | 128/290 |
| 3,411,504 | 11/1968 | Glassman | 128/290 |
| 3,559,650 | 2/1971 | Larson | 128/290 |
| 3,575,174 | 4/1971 | Mogor | 128/290 |
| 3,736,931 | 6/1973 | Glassman | 604/385 |
| 4,059,114 | 11/1977 | Richards | 128/28 |

FOREIGN PATENT DOCUMENTS

| | | | |
|---|---|---|---|
| 0091412 | 3/1983 | European Pat. Off. | 604/385 A |
| 0136524 | 4/1985 | European Pat. Off. | |

*Primary Examiner*—John D. Yasko
*Attorney, Agent, or Firm*—P. A. Leipold; D. L. Traut; J. J. Duggan

[57] ABSTRACT

A sanitary napkin is provided which minimizes the probability of side staining or side leakage by using embossed channels which are located adjacent to the longitudinal edges of the napkin. These embossed channels are activated during use by the thighs, allowing the sides of the napkin to fold upwards during use, thus forming an occlusive container.

6 Claims, 2 Drawing Figures

REDUCED LEAKAGE MENSTRUAL PAD WITH BUILT-IN FOLD LINES

TECHNICAL FIELD

The present invention relates, generally, to the field of sanitary napkins for personal feminine care or protection in order to absorb or otherwise contain menstrual fluids or similar exudate, perhaps urine, as the consequence of minor incontinence, or the like. The present invention relates more especially to an absorbent sanitary napkin for feminine hygiene, which is intended for use as an undergarment protector for absorbing flow during periods as well as between menstrual periods. This sanitary napkin forms an occlusive container to help reduce the incidence of side leakage. Most particularly, the present invention concerns an absorbent sanitary napkin with fold lines or embossed channels which are located on each side of the longitudinal axis of the sanitary napkin and which direct the folding of the side edges of the pad in an upward direction when activated by the wearer's thighs during use, thus providing a highly efficient catamenial device.

DESCRIPTION OF THE BACKGROUND ART

All manner and variety of devices or appliances configured for the absorption of such body fluids as menses are, of course, well known. Sanitary napkins are the most frequently used of these devices.

The effect of fluid run-off is apparent in all forms of sanitary napkins including those having increased absorbency and designed for heavy flow. It has been suggested that at least 20-25% of all sanitary napkins leak. To prevent this situation it is necessary to make many inconvenient pad changes at short intervals.

Thus, there have been several attempts in the art to minimize the undesirable side leakage problem associated with the use of sanitary napkins.

In U.S. Pat. No. 4,397,644 to Kimberly-Clark Corporation, there is described a sanitary napkin for feminine hygiene, which is capable of transmitting viscous menstrual fluid into the absorbent portion of the napkin to minimize cover run-off. The napkin has a fluid permeable cover which is integrated with a portion of the absorbent matrix. The sanitary napkin may be in the form of a thin sanitary napkin, mini-pad or liner, thereby extending its use as an undergarment protector to the time between menstrual periods.

The art has also offered several types of feminine protection devices which provide embossed lines for a variety of purposes. U.S. Pat. No. 3,395,201 describes a sanitary napkin wherein the longitudinal edge portions of the assemblage are bonded and the fiber density increased so that the longitudinal edge portions are stabilized. The edge portions provide strength and will not allow the short fibers to sift through the edges of the assemblage.

The technique of compressing the edges of a sanitary napkin was used in U.S. Pat. No. 3,559,650 to hold the pad and backing together while at the same time retarding the flow of fluid outwardly from the central longitudinal axis of the pad and retaining such fluid in the bulky portion of the pad.

U.S. Pat. No. 2,064,431 discloses a sanitary napkin wherein a pair of slits are provided at each end of the pad to allow the ends of the napkin to curve up when being worn.

Several patents have recognized the advantage of using embossed lines near the center of the pad. U.S. Pat. No. 3,411,504 describes a sanitary napkin which has in the top effective surface thereof, at least two longitudinal grooves or channels that lie in the mid-portion of the napkin and extend towards but terminate short of the extreme end portions of the napkin. U.S. Pat. No. 4,059,114 describes a disposable shield for garment protection having a very thin, lightweight, highly absorbent structure. The disposable shield contains one or more sets of embossed lines located near the center of the pad.

U.S. Pat. No. 3,575,174 discloses a sanitary napkin formed into a curved or tapered configuration which is structurally stabilized in that form by a pair of longitudinally extending channels embossed into the napkin from the top surface. Structural stability of the sanitary napkin in the transverse direction is also provided by forming deeply embossed channels adjacent to each end of the sanitary napkin, which channels interconnect the ends of the longitudinally embossed channels.

U.S. Pat. No. 2,787,271, however, describes a sanitary napkin having a pair of lateral flaps which are adapted to fold downwardly and bear against the opposed inner surfaces of the thighs of the wearer, for arresting any overflow once it has occurred.

The prior art has not attempted to develop an occlusive container out of the sanitary napkin to eliminate leakage. Embossed channels have been suggested yet they are not designed to allow the sides of the sanitary napkin to fold upwards during use.

OBJECTS OF THE INVENTION

Thus, it is a primary object of the invention to provide an improved sanitary napkin which minimizes the possibility of side staining or side leakage, that is, fluid run-off beyond the peripheral portions of the sanitary napkin.

It is another object of the invention to provide such an improved sanitary napkin wherein the sanitary napkin forms an occlusive container when worn.

Still another object of the present invention is to provide a sanitary napkin wherein the embossed channels adjacent the longitudinal edge of the sanitary napkin fold upward when worn thereby forming a space such that a portion of the pad is set apart from the wearer's body during use.

A further object of the invention is to provide such an improved sanitary napkin which has embossed channels located adjacent to the longitudinal sides of the sanitary napkin wherein the sides of the napkin fold up when worn thereby forming an occlusive container during use.

SUMMARY OF THE INVENTION

It has now been determined in accordance with the present invention that a sanitary napkin can be provided which minimizes the possibility of side staining or side leakage by using embossed channels which are located adjacent to the longitudinal edges of the sanitary napkin, that is, on each side of the longitudinal axis of the sanitary napkin. Advantageously, these embossed channels are activated during use by the thighs, allowing the sides of the napkin to fold upwards. Further advantageous as a particular consequence of these novel embossed channels, is the formation of an occlusive container by the sanitary napkin.

BRIEF DESCRIPTION OF THE DRAWINGS

This invention can better be understood by references to the drawings in which.

DETAILED DESCRIPTION OF THE PREFERRED EMBODIMENTS

The present invention relates, generally, to sanitary napkins for personal feminine care or protection in order to absorb or otherwise contain menstrual fluids or similar exudate, perhaps urine, as a consequence of minor incontinence, or the like. The present invention relates more especially to a sanitary napkin comprising a flexible, fluid impermeable backing sheet, a layer of absorbent material on said backing sheet, and a fluid-permeable cover having embossed on the user side face thereof a pair of embossed channels, said embossed channels located on each side of the longitudinal axis of the sanitary napkin with each of the ends of the embossed channels spaced from the side edge and longitudinal edge of the sanitary napkin, such that in use the channels are held apart from the wearer's body and are adapted to form an occlusive container during use. Accordingly, the present invention will now be described with reference to certain preferred embodiments within the aforementioned contexts; albeit, those skilled in the art will realize that such a description is meant to be exemplary only and should not be deemed limitative respecting the scope of the present invention.

Figure 1:
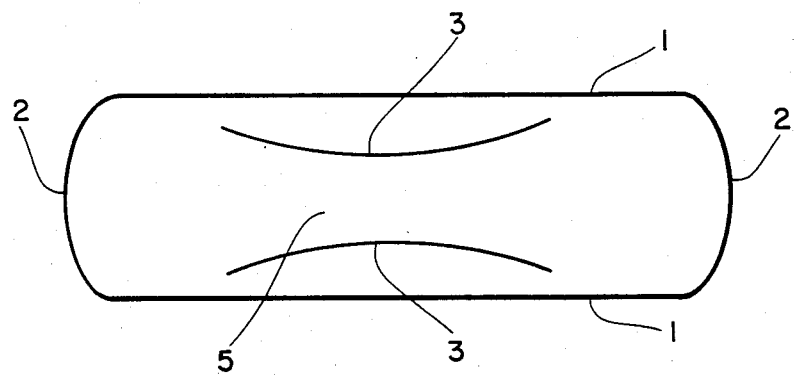
FIG. 1 is a plan view of the top of a sanitary napkin according to this invention.

Turning to the Figures of Drawing, in each of which like parts are identified with like reference characters, FIG. 1 illustrates a plan view of the top of a sanitary napkin according to this invention. The embossed channels or fold lines 3 are depicted as arcuate and are located adjacent to the longitudinal sides 1 of the sanitary napkin.

The length of the napkins is not critical. The various layers of the sanitary napkin of the present invention having the embossed channels may be any of those materials well-known in the art. The pad comprising the central layer may comprise any of the well-known materials or composites thereof used in absorbent pads including wood pulp fluff, multiple layers of cellulose wadding, cotton or rayon fibers, cellulose sponge, hydrophilic synthetic sponge such as polyurethane, and the like. It is preferred that at least some of the absorbent material in the sanitary napkin contain fusible fibers. The fusible fibers promote sealing by fusing to the baffle and/or the microfibrous layer itself. Particularly preferred is a mat which is made of coformed material. A coformed material is described in U.S. Pat. No. 4,100,324. This non-woven material has a fabric-like finish and is made up of an air-formed matrix of thermoplastic polymeric fibers having an average diameter of less than about 10 microns, this diameter is in the microfiber range, with a multiplicity of individualized wood pulp fibers dispersed throughout the matrix and serving to space these microfibers from each other. The material is formed by initially utilizing a primary air stream with the meltblown microfibers and a secondary air stream containing wood pulp fibers and merging the two air streams under turbulent conditions and subsequently the integrated air stream along a forming surface. The fabric-like appearance of this material provides a visually appealing absorbent. Also inherent in the coformed material is increased resiliency when compared to conventional cellulosic absorbents. The inclusion of fusible fiber, while having the advantages previously indicated, does reduce the absorbency of the coformed mat. The inclusion of a layer of microfibrous thermoplastic web, however, in conjunction with coformed material produces a sanitary napkin having superior absorbent capability.

The cover of the sanitary napkin may be spunbonded polypropylene or any number of other materials which allow the ready passages of fluid through the absorbent, as used in some conventional sanitary napkins.

The napkin of the present invention may be of any thickness and may cover periods of light or heavy flow. In particular, the fold lines of the present invention are suitable for a thin pad which generally has a thickness of between about 5 to 15 mm at its thickest point. The absorbency of these thin pads is comparable to that of the conventional heavy flow napkins now commercially available.

In particular, the embossed channels 3 of the present invention are well-suited for application onto the sanitary napkin claimed in U.S. Pat. No. 4,397,644 which is hereby incorporated by reference. This patent provides a sanitary napkin which is capable of transmitting viscous menstrual fluid into the absorbent portion of the napkin without cover runoff. The napkin has a fluid permeable cover which is integrated with a portion of the absorbent matrix. This portion of the absorbent matrix is designed to provide increased comfort, initially during use, and after the napkin becomes wet.

The fold lines 3 which are embossed channels adjacent to the longitudinal edges 1 are formed by compressing the layers of the pad a sufficient amount to remain intact throughout the intended use of the pad. It is relevant to note that these embossed channels or fold lines 3 are not barrier lines, that is, lines which are intended to stop the flow of body fluids beyond their boundary. Rather, the embossed channels 3 of the present invention are designed to reduce leakage by pooling body fluids during use. These fold lines may be produced in any manner such as by the application of heat, including hot calendar embossing or by ultrasonic means. The width of the embossed channels should be such that the napkin is not cut during embossing nor so wide as to allow the fluid to gather. Preferably, the width of the embossed channels or fold lines may range from about 0.020 inch to about 0.250 inch.

The embossed channels 3 along each longitudinal side 1 of the pad may be a straight line running parallel to the length of the pad and extending the length of the pad or, preferably, the embossed channel may be arcuate wherein the midpoint of the arc of the embossed channel is the greatest distance from the longitudinal edge 1 of the pad as demonstrated in FIG. 1. The embossed channels 3 may extend almost the complete longitudinal length 1 of the pad. That is, the embossed channels 3 may not extend any closer than ⅛ inch from the end edge 2 of the sanitary napkin. The embossed channels may not be any closer than ⅛ inch from the longitudinal edge 1 of the pad at any point.

If the straight-line embossed channel is any closer than ⅛ inch from the longitudinal edge 1 of the pad, it is unlikely that the embossed channel will be sufficient to direct the edge of the pad upward, and in any event, less than ⅛ inch would likely be insufficient to form an occlusive container to reduce the incidence of side leakage. The linear embossed channels are generally both parallel to each other and parallel to the longitudinal edge 1 of the sanitary napkin. However, the embossed channels need not be aligned in that fashion and may be offset.

The arcuate embossed channels are spaced inwardly of the longitudinal axis of the user side face surface of the sanitary napkin. That is, the area near the center of the arcuate embossed channels are the greatest distance from the longitudinal edge of the sanitary napkin. In the case of the arcuate embossed channel 3, if the embossed channel 3 is allowed to extend any closer than ⅛ inch from the longitudinal edge of the pad, the embossed channel 3 may actually act to direct the body fluids from the central pad 5 off the sanitary napkin.

The embossed channels 3, whether linear or arcuate, are generally symmetrical, that is, they are essentially a mirror image of each other if the pad is cut down the middle.

Figure 2:
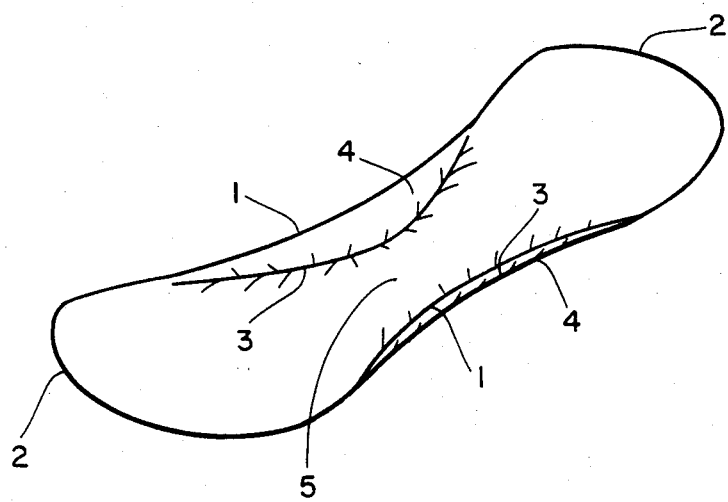
FIG. 2 is a perspective of the top of a sanitary napkin wherein the side flaps on each side of the embossed channels are folded upward.

FIG. 2 is a perspective of the top of a sanitary napkin wherein the side flaps 4 on each side of the embossed channels 3 are folded upward.

The purpose of the embossed channels 3 are to enhance the sides of the pad 4 flipping up when squeezed by the upper thighs of the wearer. The embossed channels are not barrier lines. Wells are formed and an occlusive container is formed thereby allowing the sanitary napkin to hold more exudate while minimizing side leakage of fluid from the central region of the sanitary napkin.

When the napkin is worn, overflow from the central pad 5 will advantageously be absorbed by lateral flaps 4 protecting the clothing against being soiled and giving the wearer increased confidence in avoiding embarrassing occurrences. The pad itself may be a uniform width. Alternatively, the sanitary napkin could have an hourglass shape or other shape and the same advantages could thereby be obtained. In the case of the hourglass shaped sanitary napkin, the width of the pad is less in the central region of the sanitary napkin.

While the invention has been described with reference to several preferred embodiments and illustrated with regard to a range of optional features, those skilled in the art will appreciate that various substitutions, omissions, modifications, and changes may be made without departing from the spirit hereof. Accordingly, it is intended that the foregoing descriptions be deemed merely exemplary of the preferred scope of the present invention and not to be deemed a limitation thereof.

We claim:

1. A samitary napkin comprising a flexible, fluid impermeable backing sheet, a layer of absorbent material on said backing sheet and a fluid permeable cover having embossed in the absorbent on the user side face surface thereof a pair of embosed channels, said embossed channels located on each side of the longitudinal axis of said sanitary napkin with each of the neds of said embossed channels spaced apart from the edge of said sanitary napkin at least ⅛ inch, said channels in use being spaced apart from the napkin wearer's body and allowing said napkin edges to fold upward at said embossed channels to form an occlusive volume between said napkin and the wearer's body.

2. A sanitary napkin according to claim 1 wherein said cover is embossed with a plurality of pairs of embossed channels.

3. The napkin of claim 1 wherein the longitudinal edges are linear and said channels are arcuate whereby said napkin conforms with wearer's body.

4. A sanitary napkin comprising a flexible fluid impermeable backing sheet, a layer of absorbent material on said backing sheet, and a fluid permeable cover having embossed on the user side face surface thereof at least one pair of embossed channels extending into said cover and said absorbent, said embossed channels being arcuate in a mirror image configuration with the closest points of the arcs in the middle of said napkin, said embossed channels having their ends spaced inward from the edge of said napkin at least ⅛ inch, and adapted to allow the edges to turn upward when in use to form an occlusive volume in between said napkin and the wearer's body, wherein the upward folded edges are absorbent and are provided with said fluid-impervious backing sheet and wherein during use of said napkin the embossed channels are adapted to be activated by the thighs of the wearer to allow the absorbent edges to fold upwards to form said occlusive volume between the wearer's body and said napkin.

5. The napkin of claim 4 wherein said embossed channels are between about 0.020 inch and about 0.250 in width.

6. The napkin of claim 4 wherein said napkin is provided with one pair of embossed channels.

* * * * *